United States Patent [19]

Frankel et al.

[11] Patent Number: 4,761,250

[45] Date of Patent: Aug. 2, 1988

[54] PROCESS FOR PREPARING 1,5-DIAZIDO-3-NITRAZAPENTANE

[75] Inventors: Milton B. Frankel, Tarzana; Edward F. Witucki, Van Nuys, both of Calif.

[73] Assignee: Rockwell International Corporation, El Segundo, Calif.

[21] Appl. No.: 764,048

[22] Filed: Aug. 9, 1985

[51] Int. Cl.$^4$ .................... C07C 117/00; C06B 25/34
[52] U.S. Cl. .................. 260/349; 558/487; 149/92
[58] Field of Search .......... 149/92; 260/349; 558/480, 487

[56] References Cited

U.S. PATENT DOCUMENTS

| | | | |
|---|---|---|---|
| 4,427,466 | 1/1984 | Flanagan et al. | 149/92 |
| 4,440,687 | 4/1984 | Witucki et al. | 260/349 |
| 4,450,110 | 5/1984 | Simmons et al. | 149/92 |
| 4,472,311 | 9/1984 | Frankel et al. | 260/349 |

Primary Examiner—John F. Terapane
Assistant Examiner—Catherine S. Kilby
Attorney, Agent, or Firm—H. Fredrick Hamann; Harry B. Field; David C. Faulkner

[57] ABSTRACT

A process for producing 1,5-diazido-3-nitrazapentane (DANPE) which comprises the steps of nitrating diethanolamine with nitric acid in a halogenated solvent such as methylene chloride to form 1,5-dinitrato-3-nitrazapentane (DINA) as intermediate, solvent transferring such intermediate from the halogenated solvent to dimethylsulfoxide, adding sodium azide to the resulting solution to form DANPE as product, and solvent transferring such product from the dimethylsulfoxide to another halogenated solvent, e.g. methylene chloride. Thus, both DINA intermediate and DANPE product are prepared in solution, and both can also be purified in solution, eliminating the necessity for isolating the neat, hazardous compounds. The DANPE product can be further solvent transferred from the halogenated solvent to ethyl acetate to form an ethyl acetate solution of DANPE, which can be used to furnish the DANPE as an energetic plasticizer, e.g. in the production of gun propellants.

16 Claims, No Drawings

PROCESS FOR PREPARING 1,5-DIAZIDO-3-NITRAZAPENTANE

BACKGROUND OF THE INVENTION

1. Field of the Invention

This invention relates to production of 1,5-diazido-3-nitrazapentane, and is particularly directed to an improved process for producing this compound.

2. Description of the Prior Art

Solid propellants are formulated from an oxidizer and fuel together with suitable binders and plasticizers to impart physical integrity. Most highly energetic systems utilize binders and plasticizers containing energetic groups such as nitro ($-NO_2$), fluorodinitro ($FC(NO_2)_2-$), difluoroamino ($-NF_2$), and many others.

Utilization of azido plasticizers has become a reality during the last several years. These azido plasticizers impart additional energy to propellants since each azido group present adds approximately 85 kcal/mole of energy to the system.

One functionally terminated azido compound of this type, 1,5-diazido-3-nitrazapentane (DANPE), together with its method of preparation, has been disclosed as an energetic plasticizer for use in solid propellants, gun propellants and explosives, in U.S. application Ser. No. 270,453, filed June 4, 1981, by Joseph E. Flanagan et al.

Such compounds can be prepared by the nitration of diethanolamine (DEA) to 1,5-dinitrato-3-nitrazapentane (DINA) and then treating the latter dinitrato compound with ionic azide to give the desired 1,5-diazido-3-nitrazapentane (DANPE), according to the following reactions:

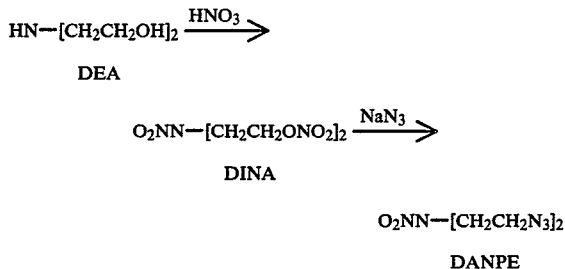

In the above process, the solid DINA is isolated and purified, prior to conversion to the DANPE. However, since DINA was classified as a class A explosive by the Bureau of Safe Transportation, and the DANPE is also a class A explosive, the presently practiced synthetic process is considered too hazardous for commercial operations. It is accordingly desirable to handle these materials in a desensitized form, i.e., in solution.

SUMMARY OF THE INVENTION

There is accordingly provided by the present invention a process for producing 1,5-diazido-3-nitrazapentane (DANPE) which comprises the steps of nitrating diethenolamine with nitric acid in a halogenated solvent such as methylene chloride, to form 1,5-dinitrato-3-nitrazapentane (DINA), solvent transferring the DINA from the halogenated solvent to dimethylsulfoxide (DMSO), or other suitable solvent such as dimethylformamide, adding sodium azide to the resulting DINA/DMSO solution to form 1,5-diazido-3-nitrazapentane (DANPE) and solvent transferring the DANPE from the dimethylsulfoxide solvent to another halogenated solvent.

The process also includes the steps of purifying the DINA intermediate in solution in the first halogenated solvent and purifying the DANPE product in solution in the other halogenated solvent.

If desired, the process can include the step of further solvent transferring the DANPE from the halogenated solvent to ethyl acetate to produce a DANPE/ethyl acetate solution, which is preferred for use in providing an energetic plasticizer for certain applications, as hereinafter noted.

Thus, the 1,5-diazido-3-nitrazapentane product is produced according to the invention by preparing and purifying both the intermediate 1,5-dinitrato-3-nitrazapentane and the product, in solution, and the improved procedure can be safely scaled-up to commercial production.

OBJECTS OF THE INVENTION

It is accordingly one object of the present invention to provide an improved process for the preparation of 1,5-diazido-3-nitrazapentane.

Another object of the present invention is the provision of a process for preparing 1,5-diazido-3-nitrazapentane in which the intermediate compound 1,5-dinitrato-3-nitrazapentane, is prepared and purified in solution prior to reaction with the azide to give the desired 1,5-diazido-3-nitrazapentane.

A particular object of the invention is the provision of an improved process of the above type in which both the intermediate 1,5-dinitrato-3-nitrazapentane (DINA) and the final product 1,5-diazido-3-nitrazapentane (DANPE) are prepared and purified in solution utilizing solvent transfer operations, and eliminating the necessity for isolating the neat hazardous compounds.

These and other objects and features of the present invention will be apparent from the following detailed description.

DESCRIPTION OF THE PREFERRED EMBODIMENTS 1,5-dinitrato-3-nitrazapentane is first prepared by reacting diethanolamine with nitric acid. The reaction is carried out in a halogenated solvent, particularly chlorinated hydrocarbon solvents, such as methylene chloride, carbon tetrachloride, chloroform or ethylene dichloride. The preferred halogenated solvent is methylene chloride.

The reaction is preferably carried out in the presence of hydrochloric acid as catalyst for the nitration and acetic anhydride, which functions to take up water.

In carrying out the reaction, the nitric acid usually is employed in excess of the diethanolamine (DEA), utilizing a molar proportion of nitric acid to DEA ranging from about 6 to 1, to about 2 to 1, preferably about 3:1. The amount of acetic anhydride employed can range from about 2 to about 10, preferably about 4, moles per mole of DEA, and only a small catalytic amount of hydrochloric acid is utilized ranging from about 2 to about 10 grams per mole of DEA.

In preferred practice the nitric acid and diethanolamine are added gradually, e.g. dropwise, to the halogenated solvent, e.g. methylene chloride, solution of acetic anhydride and hydrochloric acid. The temperature during this addition is held between about 0° C. to about 40° C., preferably about 20°–25° C., and after the addition is completed the reaction mixture is warmed to about 40° C., to ensure complete reaction for production of 1,5-dinitrato-3-nitrazapentane (DINA).

After cooling the reaction mixture, e.g. to ambient temperature, cold water is added to the reaction mixture, forming an aqueous layer and an organic layer, the DINA being dissolved in the organic layer.

The layers are separated and the aqueous layer is extracted with halogenated solvent, such as methylene chloride. The organic portions are combined and washed with sodium bicarbonate and finally with water until the final washing tests neutral. The organic portion is then diluted with halogenated solvent, e.g. methylene chloride, and passed through a chromatographic columns of $SiO_2$, to remove color.

The DINA is then solvent transferred from halogenated solvent to dimethylsulfoxide (DMSO). For this purpose DMSO is added to the DINA/methylene chloride solution and the methylene chloride is removed from the resulting solution by application of a vacuum, leaving 1,5-dinitrato-3-nitrazapentane (DINA) in solution in DMSO, the amount of DMSO employed being such as to form a 20-30% solution of DINA in DMSO. In preferred practice, removal of methylene chloride and addition of DMSO are carried out in stages to facilitate substantially complete final removal of the methylene chloride and its replacement by DMSO.

Sodium azide ($NaN_3$) is then added to the DINA/DMSO solution, in an amount such as to produce a 5-20% excess of $NaN_3$ over DINA. The reaction mixture is heated to a temperature in the range of about 50° to about 90° C., preferably about 80° to about 90° C. for a period sufficient to convert the DINA to the 1,5-diazido-3-nitrazapentane (DANPE) product. After cooling, a halogenated solvent, e.g. methylene chloride, and in an amount which can be approximately equivalent to the amount of the DMSO in the reaction mixture, is added to the reaction mixture and the entire organic portion is washed with water to remove DMSO. The resulting halogenated solvent solution of 1,5-diazido-3-nitrazapentane is then passed through a $SiO_2$ column which removes color. The resulting solution is then passed through a basic alumina column for further purification.

In place of dimethylsulfoxide, any suitable solvent can be used having a boiling point higher than the temperature of the reaction between DINA and the sodium azide, preferably greater than 90° C., and which dissolves both reactants, and which, following the reaction, can be washed out with water. Thus, for example, dimethylformamide (DMF) alternatively can be employed.

Where the DANPE product is to be used as an energetic plasticizer in the production of gun propellants, since ethyl acetate is a preferred solvent for formulating gun propellants where nitrocellulose is employed as a major component, the DANPE product in the halogenated solvent solution can be solvent transferred from the halogenated hydrocarbon in the final solution to ethyl acetate. This is accomplished by adding ethyl acetate to the latter solution in an amount which can be approximately equivalent to the amount of halogenated solvent. The halogenated solvent, e.g. methylene chloride, is then distilled off, leaving the DANPE product in solution in the preferred ethyl acetate as solvent. The resulting solvent solution can be stored and/or transported, as desired, to provide DANPE in a desensitized form as an energetic azido plasticizer in the manufacture, for example, of gun propellants, without the necessity for isolating the neat hazardous compound.

The following are examples of practice of the process of the invention, but it will be understood that such examples are only illustrative and not limitative of the invention.

EXAMPLE I

A. Preparation of Dinitroxydiethylnitramine (DINA)

A mixture of 850 g acetic anhydride and 10 g of 37% hydrochloric acid was cooled in a reactor to 5° C. 424.4 g (6.4 moles) of nitric acid was charged to one addition funnel and 10% of it was added initially to the reactor. 400 mls methylene chloride was then added and the other addition funnel was charged with 210 g (2 moles) of diethanolamine. The nitric acid and diethanolamine were then added dropwise simultaneously, keeping the nitric acid content in the reactor slightly in excess of the diethanolamine. The addition required 45 minutes and the temperature during this addition was held at 20°-25° C. with cooling. After the addition was completed, the reaction mixture was warmed to and held at 40° C. for 10 minutes to ensure complete reaction.

After cooling to ambient temperature, 650 mls of cold water was added carefully at which time two layers appeared. The temperature at this point was 15° C. No solid DINA was encountered at any time. The layers were separated and the aqueous portion was extracted twice with 100 mls methylene chloride each time. The combined organic portions were then washed with water, sodium bicarbonate, and finally again with water. The pH of the washings were neutral at this point. The organic portion was then diluted to 1000 ml with methylene chloride and passed through a chromatographic column of $SiO_2$ (10"×2" dia). Much of the color was removed in this step. A sample was taken at this point and the yield of DINA determined to be 80%.

B. Preparation of Diazidodiethylnitramine (DANPE)

Before this preparation was carried out, DINA formed in the previous step was solvent transferred from methylene chloride to dimethylsulfoxide (DMSO). One liter of a methylene chloride solution containing approximately 307 g (1.28 moles) of DINA was charged along with 200 mls of DMSO to the reactor containing a small Claisen take-off head. Vacuum was applied gently and methylene chloride was removed to a cooled trap. When 70% of the methylene chloride was removed 200 more mls of DMSO was added. Samples were removed periodically to determine the methylene chloride content of the pot, which was monitored by gas chromatography. Final methylene chloride content was 0.5%. DINA remained in solution throughout the transfer.

DMSO was again added at this point, bringing the final total to 950 mls of DMSO, the Claisen head was removed, and the azide reaction was carried out. For this purpose, 187 g (2.88 moles) of $NaN_3$ was added and the reaction mixture was heated to and held at 85° C. for 16 hours. After cooling an equal quantity of $CH_2Cl_2$ solvent was added and the entire organic portion was washed six times with water to remove DMSO. G.C. (gas chromatography) analysis at this point indicated that DMSO had been completely removed.

The $CH_2Cl_2$ solution was then passed through a small $SiO_2$ column which removed a substantial quantity of color. A sample was removed to determine yield and purity. The yield at this point was 230 g (90%) and the purity was approximately 95% ($nD^{23}$ 1.5205; ref: 1.5259). The impurity contained an undesirable carbonyl group. To remove this impurity 1700 mls of the $CH_2Cl_2$ solution was passed through a basic alumina column (10"×2" dia) and rinsed with another 1400 mls of the same solvent. The impurity was retained on the column and final yield of DANPE in the eluent was 210 g, 82% yield. Its purity as determined by G.C. was 99% ($nD^{23}$ 1.5246).

EXAMPLE II

The DANPE present in the $CH_2Cl_2$ solution formed in Example I was solvent transferred from the methylene chloride to ethyl acetate. For this purpose, 1,000 mls of the $CH_2Cl_2$ solution containing about 200 g of DANPE was charged along with 1,000 mls of ethyl acetate to a vessel. Vacuum was applied, distilling off the methylene chloride solvent, which was recovered in a cooled trap. Samples were removed periodically from the vessel to determine the helogenated solvent content. The final solution remaining in the vessel contained DANPE dissolved in ethyl acetate.

EXAMPLE III

The procedure of Example I is substantiallly followed but employing ethylene dichloride in place of methylene chloride in Example I, Part A, and in the same amount. Also, dimethylformamide (DMF) is employed in place of and in the same amount as the DMSO of Example I, Part B.

The results obtained are similar to those obtained in Example I.

From the foregoing, it is seen that the invention provides an improved method for the preparation and purification in solution of 1,5-diazido-3-nitrazapentane product from the intermediate 1,5-dinitrato-3-nitrazapentane, without requiring the isolation of either of the compounds and hence permitting preparation of the product by the invention procedure safely in production quantities.

It is to be understood that what has been described is merely illustrative of the principles of the invention and that numerous arrangements in accordance with this invention may be devised by one skilled in the art without departing from the spirit and scope thereof.

What is claimed is:

1. A solvent process for making 1,5-diazido-3-nitrazapentane comprising the sequential steps of
   nitrating diethanolamine with nitric acid in a first halogenated solvent to make the intermediate 1,5-dinitrato-3-nitrazapentane,
   solvent transferring said intermediate from the first halogenated solvent to a second solvent selected from the group consisting of dimethylsulfoxide and dimethylformamide,
   reacting said intermediate with sodium azide to form 1,5-diazido-3-nitrazapentane as product in said second solvent, and
   solvent transferring said product from said second solvent to a third halogenated solvent.

2. The process of claim 1, including the steps of purifying said intermediate in solution in the first halogenated solvent and purifying said product in solution in said third halogenated solvent.

3. The process of claim 1, including the further step of solvent transferring said product from said third halogenated solvent to ethyl acetate.

4. The process of claim 1, said step of solvent transferring said intermediate comprising adding said second solvent to said first halogenated solvent solution of said intermediate, and subjecting the resulting solution to a vacuum to remove said halogenated solvent.

5. The process of claim 1, said step of solvent transferring said product comprising adding said third halogenated solvent to said second solvent solution of said product and washing the resulting solution with water to remove said second solvent, and leaving said product in solution in said third halogenated solvent.

6. The process of claim 1, said first and third halogenated solvents comprising methylene chloride.

7. The process of claim 1, said second solvent being dimethylsulfoxide.

8. The process of claim 6, said second solvent being dimethylsulfoxide, and including the steps of purifying said intermediate and said product in solution in said methylene chloride.

9. The process of claim 8, including the further step of solvent transferring said product from said methylene chloride to ethyl acetate by adding ethyl acetate to said methylene chloride solution of said product, and distilling off said methylene chloride, and leaving said product in solution in said ethyl acetate.

10. A process for making 1,5-diazido-3-nitrazapentane from 1,5-dinitrato-3-nitrazapentane, both of said compounds being prepared in solution, comprising the steps of
    nitrating diethanolomine with nitric acid in a first halogenated solvent selected from the group consisting of methylene chloride, carbon tetrachloride, chloroform and ethylene dichloride, employing an excess of nitric acid, and in the presence of acetic anhydride and hydrochloric acid, to make the intermediate 1,5-dinitrato-3-nitrazapentane,
    solvent transferring said intermediate from the first halogenated solvent to dimethylsulfoxide, by adding dimethylsulfoxide to the first halogenated solvent solution of said intermediate and subjecting the resulting solution to a vacuum to remove said first halogenated solvent, and leaving a solution of said intermediate in dimethylsulfoxide,
    adding sodium azide to said halogenated solvent solution of said intermediate, in an amount such as to produce a 5–20% excess of $NaN_3$ over said intermediate, and heating the resulting solution to a temperature of about 50° to about 90° C. to form 1,5-diazido-3-nitrazapentane as product, and
    solvent transferring said product from the dimethylsulfoxide to a second halogenated solvent selected from the group consisting of methylene chloride, carbon tetrachloride, chloroform and ethylene dichloride, by adding said second halogenated solvent to said dimethylsulfoxide solution of said product, and washing the resulting solution with water to remove dimethylsulfoxide, and leaving said product in solution in said second organic solvent.

11. The process of claim 10, including the steps of purifying said intermediate in solution in the first halogenated solvent and purifying said product in solution in said second halogenated solvent.

12. The process of claim 11, said first halogenated solvent comprising methylene chloride.

13. The process of claim 12, said second halogenated solvent comprising methylene chloride, and including the further step of solvent transferring said product from said methylene chloride to ethyl acetate, by adding ethyl acetate to said methylene chloride solution of said product and distilling off said methylene chloride, leaving an ethyl acetate solution of said product.

14. In a process for making 1,5-diazido-3-nitrazapentane from the intermediate 1,5-dinitrato-3-nitrazapentane, by nitrating diethanolamine with nitric acid in a halogenated solvent to make said intermediate and reacting said intermediate with sodium azide at elevated temperature to form 1,5-diazido-3-nitrazapentane, the improvement which comprises the steps of solvent transferring said intermediate from said halogenated solvent to a solvent having a boiling point higher than the elevated temperature of reaction of the 1,5-dinitrato-3-nitrazapentane and sodium azide, and which dissolves both reactants and is soluble in water, and following said reaction of 1,5-dinitrato-3-nitrazapentane with sodium azide to form 1,5-diazido-3-nitrazapentane as product, solvent transferring said product from said higher boiling solvent to a halogenated solvent.

15. The process of claim 14, said higher boiling solvent having a boiling point greater than 90° C.

16. The process of claim 15, said higher boiling solvent selected from the group consisting of dimethylsulfoxide and dimethylformamide.

* * * * *